(12) United States Patent
Miller et al.

(10) Patent No.: US 11,304,689 B2
(45) Date of Patent: Apr. 19, 2022

(54) SUTURE ANCHOR COMPRISING SUTURE FILAMENT AND SUTURE TAPE

(71) Applicant: Conmed Corporation, Utica, NY (US)

(72) Inventors: Peter C. Miller, Largo, FL (US); Jeremy Reedy, Largo, FL (US)

(73) Assignee: Conmed Corporation, Utica, NY (US)

( * ) Notice: Subject to any disclaimer, the term of this patent is extended or adjusted under 35 U.S.C. 154(b) by 108 days.

(21) Appl. No.: 15/075,585

(22) Filed: Mar. 21, 2016

(65) Prior Publication Data
US 2016/0270777 A1 Sep. 22, 2016

Related U.S. Application Data

(60) Provisional application No. 62/136,557, filed on Mar. 22, 2015.

(51) Int. Cl.
*A61B 17/04* (2006.01)

(52) U.S. Cl.
CPC .. *A61B 17/0401* (2013.01); *A61B 2017/0406* (2013.01); *A61B 2017/0409* (2013.01); *A61B 2017/0459* (2013.01)

(58) Field of Classification Search
CPC ........ A61B 17/0401; A61B 2017/0406; A61B 2017/0409; A61B 2017/459
USPC .................................................. 606/151, 232
See application file for complete search history.

(56) References Cited

U.S. PATENT DOCUMENTS

| | | | |
|---|---|---|---|
| 3,464,415 A * | 9/1969 | Brownlee | A61F 13/00008 604/362 |
| 4,244,369 A * | 1/1981 | McAvinn | A61F 13/44 604/362 |
| 9,381,013 B2 | 7/2016 | Daniel | |
| 2006/0178683 A1 * | 8/2006 | Shimoji | A61B 17/07207 606/151 |
| 2012/0283749 A1 | 11/2012 | Sauer | |
| 2013/0116799 A1 * | 5/2013 | Derwin | A61L 27/48 623/23.72 |
| 2013/0190819 A1 * | 7/2013 | Norton | A61B 17/0485 606/232 |
| 2013/0237997 A1 * | 9/2013 | Arai | A61B 17/0401 606/144 |
| 2013/0282034 A1 * | 10/2013 | Chu | A61F 2/0063 606/151 |

(Continued)

FOREIGN PATENT DOCUMENTS

| | | |
|---|---|---|
| EP | 2698128 | 2/2014 |
| WO | 2012151592 | 11/2012 |

OTHER PUBLICATIONS

International Search Report and Written Opinion Form PCT/ISA/220, International Application No. PCT/US2016/023379, pp. 1-16, Dated Oct. 4, 2016.

(Continued)

*Primary Examiner* — Thomas McEvoy

(74) *Attorney, Agent, or Firm* — Bond, Schoeneck & King, PLLC; Frederick J. M. Price

(57) ABSTRACT

A suture anchor that is configured to pull repair sutures into a pre-formed hole in bone or boney tissue, having a fibrous construct having a first side and a second side; and a first filament body passing through the fibrous construct, the first filament body forming a first pair of loops that interleave with one another on one of the first side or the second side of the fibrous construct.

18 Claims, 12 Drawing Sheets

(56) References Cited

U.S. PATENT DOCUMENTS

2014/0088529 A1* 3/2014 Bengtson ............... A61F 13/36
 604/360
2015/0073441 A1* 3/2015 Fallin ................. A61B 17/0482
 606/144

OTHER PUBLICATIONS

Australian Government Examination Report No. 1 for Standard Patent Application ABN 38 113 072 755, pp. 1-4, Dated Nov. 27, 2017.

* cited by examiner

SUTURE ANCHOR COMPRISING SUTURE FILAMENT AND SUTURE TAPE

CROSS-REFERENCE TO RELATED APPLICATIONS

The present application claims priority to and the benefit of U.S. provisional patent application No. 62/136,557, filed on Mar. 22, 2015, the entire contents of which are hereby incorporated by reference.

BACKGROUND OF THE INVENTION

1. Field of the Invention

The subject matter of this disclosure relates to suture anchors, and, more particularly to, embodiments that include suture material interleaved into a soft, malleable substrate to form a loop configuration to pull repair sutures into a pre-formed hole and to deform the substrate.

2. Description of the Related Art

Surgical procedures often call for suture anchors to provide a reliable attachment location for sutures in and/or against a substrate. The attached sutures are then used to capture and retain other objects including soft tissue. The substrate may be bone or boney material or soft tissue. For bone and like boney material, suture anchors can insert into a pre-formed hole in the bone so that the attached suture extends from the suture anchor out of the pre-formed hole. Where the substrate is soft tissue, suture anchors can reside on a side of the soft tissue so that the suture extends from the suture anchor, through a hole in the tissue, and further beyond the soft tissue on a side opposite the soft anchor.

In conventional practice, suture anchors can incorporate at least one feature to generate a retention capacity to retain the suture anchor in the pre-formed hole. In some anchors, the feature embodies a ridged member that can deform to create an interference fit with the substrate. Other suture anchors utilize an external feature (e.g., a barb, screw threads(s), etc.). These external features can interact with the substrate to create the retention capacity, often by piercing, cutting, and/or deforming the substrate. In still other suture anchors, the feature may be moveable (e.g., a deployable barb) that translates to create the retention capacity.

Soft suture anchors have also been developed, such as the Biomet JuggerKnot™ (a trademark of Biomet Corporation), which utilizes a stiff braided line, which appears to function as a barb against the side of a hole in a substrate.

Many factors have a direct effect on the actual retention capacity achieved by any suture anchor. For example, the quality of tissue, bony or soft, may increase or decrease the retention capacity by a large degree depending on the design of a particular suture anchor. Thus, some suture anchors perform well in certain circumstances while other anchors perform better in other circumstances. Similarly, the quality of installation affects the retention capacity.

Accordingly, there is a need in the art for a suture material interleaved into a soft, malleable substrate to form a loop configuration to pull repair sutures into a pre-formed hole and to deform the substrate.

DESCRIPTION OF THE RELATED ART SECTION DISCLAIMER

To the extent that specific patents/publications/products are discussed above in this Description of the Related Art Section or elsewhere in this Application, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

SUMMARY OF THE INVENTION

Embodiments of the present invention recognize that there are potential problems and/or disadvantages with the conventional suture anchors as described above. Therefore, a need exists for a suture anchor to pull repair sutures into a pre-formed hole in bone or boney tissue and deform the substrate. Various embodiments of the present invention may be advantageous in that they may solve or reduce one or more of the potential problems and/or disadvantages discussed herein.

The present disclosure is directed to an inventive configuration, structure, and resulting function of a suture anchor. Various embodiments herein are directed to a suture anchor, including, but not limited to: a fibrous construct having a first side and a second side; and a first filament body passing through the fibrous construct, the first filament body forming a first pair of loops that interleave with one another on one of the first side or the second side of the fibrous construct.

According to an alternative embodiment, the anchor suture, includes, but is not limited to a substrate; and a filament interwoven into the substrate, the filament extending through the substrate at two different passing locations to form a first loop and a second loop, wherein the first loop extends through the second loop and is configured to receive repair suture therein.

According to another aspect, a suture anchoring system includes, but is not limited to, a suture anchor having a filament disposed in a loop configuration with a first loop extending through a second loop, the suture anchor having an un-deployed state and a deployed state in which the effective area of the suture anchor is different than the effective area of the suture anchor in the un-deployed state; and insertion tooling coupled with the suture anchor.

The discussion below describes embodiments of a suture anchor that is configured to pull repair sutures into a pre-formed hole in bone or boney tissue. These configurations can have a filament (e.g., a suture) interwoven into a soft, malleable substrate (e.g., suture ribbon). The interwoven filament can form loops to receive free-ends of the repair suture that originates from a fixation site adjacent the pre-formed hole. In use, tension on free-ends of the interwoven filament can translate the loops to engage the repair suture, effectively pulling the free-ends into the pre-formed hole and interleaving the repair suture with the substrate in a manner that allows the filament to freely translate through the substrate and relative to the repair suture.

BRIEF DESCRIPTION OF THE DRAWINGS

The present invention will be more fully understood and appreciated by reading the following Detailed Description in conjunction with the accompanying drawings. The accompanying drawings illustrate only typical embodiments of the disclosed subject matter and are therefore not to be considered limiting of its scope, for the disclosed subject matter may admit to other equally effective embodiments.

Reference is now made briefly to the drawings, in which.

Figure 1:
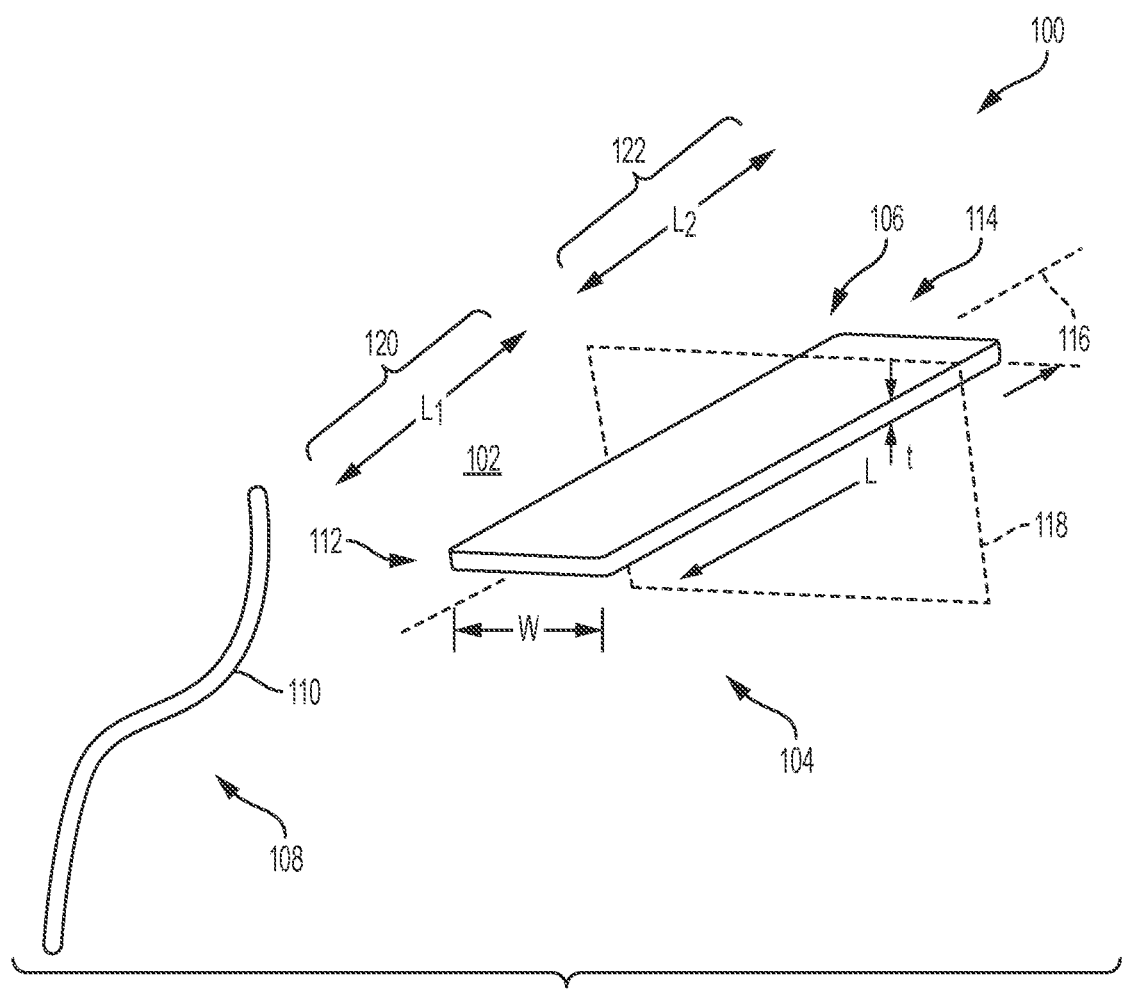
FIG. 1 represents a perspective view of an exemplary embodiment of a suture anchor in exploded form in accordance with an embodiment.

Where applicable like reference characters designate identical or corresponding components and units throughout the several views, which are not to scale unless otherwise indicated. Moreover, the embodiments disclosed herein may include elements that appear in one or more of the several views or in combinations of the several views.

DETAILED DESCRIPTION

Referring now to the drawings, wherein like reference numerals refer to like parts throughout, there is seen in FIG. 1 a perspective view of an exemplary embodiment of a suture anchor 100 in exploded form. The suture anchor 100 has a first side 102 and a second side 104. The suture anchor 100 can include a fibrous construct 106 and a filament 108, shown here as a first filament body 110 that can interweave into the fibrous construct 106, as noted more below. The fibrous construct 106 can have a first end 112, a second end 114, and a longitudinal axis 116 extending therebetween. Dimensions for the fibrous construct 106 are set out and designated as a width W, a length L, and a mattress thickness t for the generally thin, rectangular geometry shown in FIG. 1. The fibrous construct 106 also has a mid-plane 118 that is perpendicular to the longitudinal axis 116. The mid-plane 118 bisects the fibrous construct 106 to form a pair of sections (e.g., a first section 120 and a second section 122) of substantially equal length L1, L2.

The filament 108 can comprise suture material of various constructions and composites. These constructions include braided suture (with multiple filaments wound together) and single or "mono-filament" suture that consists of a single strand of suture material. The constructions can also include any other metallic or non-metallic filamentary suture, whether absorbable or non-absorbable, as desired.

The fibrous construct 106 can be configured to operate in the suture anchor 100 as the soft, malleable substrate. These configurations may benefit from construction that can deform, but that is not prone to failure (e.g., tearing) with the filament 108 under tension. The construction may utilize multiple fibers of implantable materials (e.g., ultra-high molecular weight polyethylene (UHMW), polyester, etc.). These fibers may form a structure for the substrate that is braided, woven, non-woven, knitted, and the like.

When assembled, the first filament body 110 penetrates variously through the fibrous construct 106 to form an anchor deploying structure. The anchor deploying structure has loops that interleave with one another. Tensioning free-ends of the first filament body 110 causes the loops to engage the repair suture, pull the repair suture into the pre-formed hole, and arrange the repair suture in a tortuous path within the fibrous construct 106. This tortuous path effectively locks the repair suture to prevent movement of the repair suture relative to the fibrous construct 106. Once the repair suture is locked, the first filament body 110 can translate freely relative to both the repair suture and the fibrous construct 106. In this way, further tensioning of the free-ends of the first filament body 110 can change the effective area of the fibrous construct 106. This feature is beneficial in surgical implementations to firmly secure the repair suture in the pre-formed hole. In one implementation, the suture anchor 100 assumes a first or un-deployed state with a first effective area to allow the end user (e.g., a surgeon) to insert the suture anchor 100 into the pre-formed hole. Tension on the first filament body 110 causes the suture anchor 100 to assume a second or deployed state with a second effective area that prevents the anchor 100 from exiting the pre-formed opening in the bone.

Figure 2:
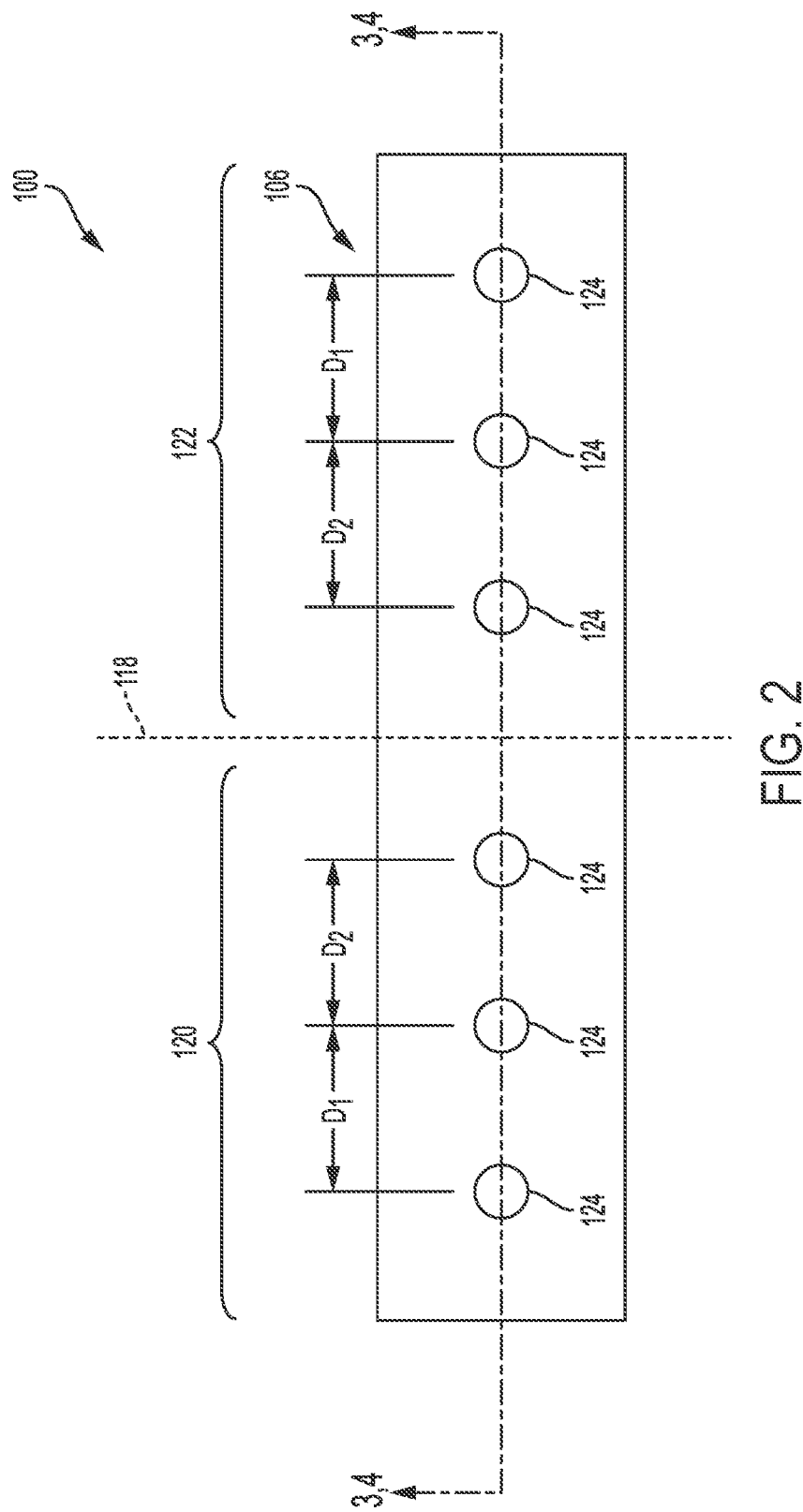
FIG. 2 represents a plan view the suture anchor of FIG. 1 with parts removed for clarity in accordance with an embodiment.

Referring now to FIG. 2, there is shown a plan view of the suture anchor 100 with the filament 108 removed for clarity. The fibrous construct 106 has one or more passing locations 124 that can receive the filament 108 (FIG. 1). The passing locations 124 embody annular openings that penetrate the material of the fibrous construct 106, although elongated slots and/or other shapes and geometry for the openings may provide additional benefits as relates to the capabilities of the suture anchor 100 contemplated herein. In the present example of FIG. 2, the passing locations 124 embody six (6) openings with three (3) openings on either side 120, 122 of the mid-plane 118. The openings may be equally-spaced from one another (wherein the distance D1 is equal to the distance D2 in the example of FIG. 2). This disclosure contemplates that the number, size, spacing, and arrangement of the passing locations 124 may vary to accommodate different materials for the fibrous construct 106 or other factors that can facilitate the capabilities of the suture anchor 100. For example, the openings may be aligned on the longitudinal axis 116, as shown, or offset laterally from the longitudinal axis 116, as desired. It is expected that some experimentation may need to balance the capabilities of the suture anchor 100 to change from the un-deployed state to the deployed state with the ability for the filament 108 (FIG. 1) to traverse through the fibrous construct 106 to engage and translate the repair suture as noted herein.

Figure 3:
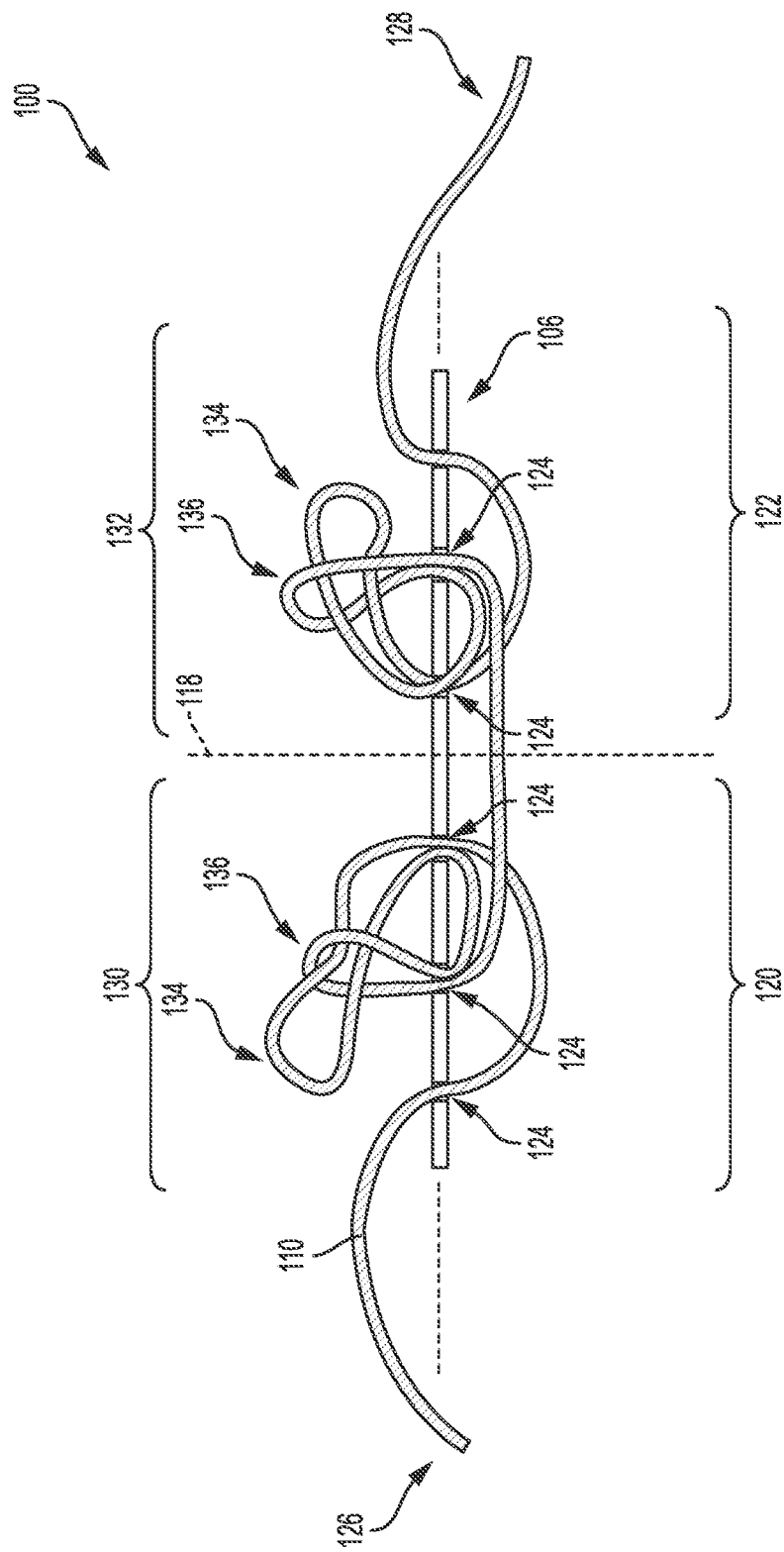
FIG. 3 represents an elevation view of the cross-section of the suture anchor of FIG. 2 in assembled form in accordance with an embodiment.
Figure 4:
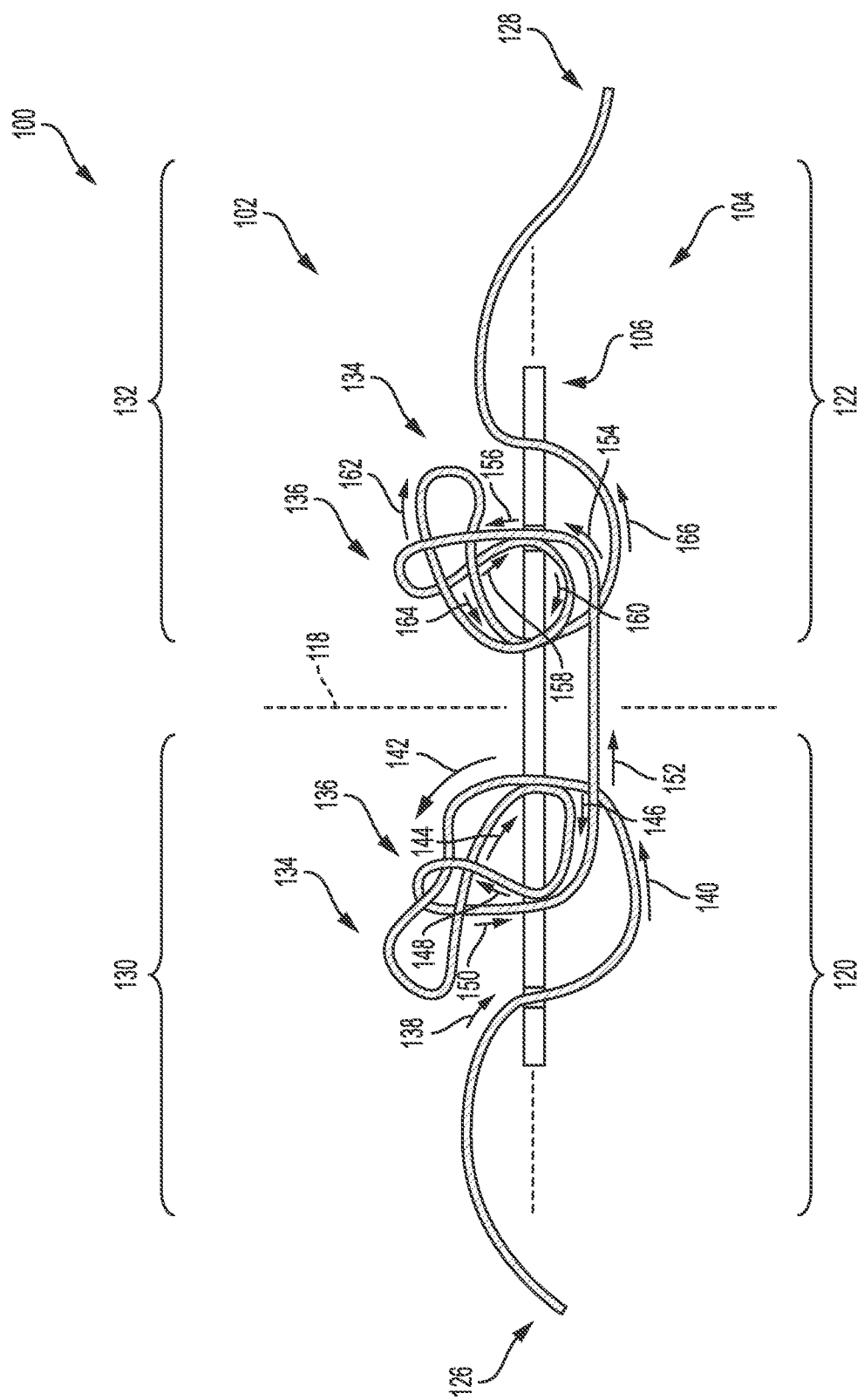
FIG. 4 represents an elevation view of the cross-section of the suture anchor of FIG. 2 in assembled form in accordance with an embodiment.

Referring now to FIGS. 3 and 4, there are shown elevation views of the cross-section of an example of the suture anchor 100 in assembled form taken at line 3,4-3,4 of FIG. 2. These diagrams depict the example prior to integration on an inserter tooling that is used to insert the suture anchor 100 into the pre-formed hole. In FIG. 3, the first filament body 110 interleaves with the fibrous construct 106, leaving a pair of free-ends (e.g., a first free-end 126 and a second free-end 128). As noted herein, the free ends 126, 128 are available for the surgeon to tension and deploy the suture anchor 100.

The first filament body 110 penetrates through the passing locations 124 in a threading pattern to forms the anchor deploying structure. The threading pattern arranges the first filament body 110 in one or more loop configurations (e.g., a first loop configuration 130 and a second loop configuration 132), one found in either section 120, 122 and on either side of the mid-plane 118. The loop configurations 130, 132 are configured to receive free-ends of repair suture (not shown) that extend from the adjacent fixation point. As also shown in FIG. 3, in the loop configurations 130, 132, the threading pattern forms the first filament body 110 into a pair of loops (e.g., a first loop 134 and a second loop 136). The loops 134, 136 integrate with one another so the first loop 134 (also "threader loop 134") extends through the second loop 136 (also "center loop 136") in the un-deployed state.

In one implementation, the threading pattern configures the threader loops 134 much longer than the center loops 136 in the un-deployed state. This configuration allows the threader loops 134 to extend out of the pre-formed hole with the suture anchor 100 resident in the pre-formed hole and prior to the suture anchor 100 being changed from its un-deployed state to its deployed state. In this way, the threader loops 134 are in a position that is not obscured from view of the surgeon. This position allows the surgeon to thread the free-ends of the repair suture (not shown) through the threader loops 134 in preparation to change the suture anchor 100 from its un-deployed to its deployed state.

FIG. 4 includes enumerated arrows to help discuss an example of the threading pattern to arrange the first filament body 110 into the fibrous construct 106. This threading pattern is helpful to interleave the first filament body 110 with the fibrous construct 106 prior to installation on the inserter tooling. Following the first filament body 110 from left to right in the diagram, and starting at the first free-end 126 of the filament body 110, at arrow 138, the first filament body 110 extends through the fibrous construct 106 from the first side 102 to the second side 104. At arrow 140, the first filament body 110 then extends back through the fibrous construct 106 from the second side 104 to the first side 102. Following arrow 140 to arrow 142 and arrow 144, the first filament body 110 forms the threader loop 134 before again extending through the fibrous construct 106 from the first side 102 to the second side 104 (after arrow 144). At arrow 146, the first filament body 110 traverses along the longitudinal axis 116 of the fibrous structure 106 on the second side 104 until extending again from the second side 104 to the first side 102. Following arrow 148 to arrow 150, the first filament body 110 forms the center loop 136 around at least part of the threader loop 134 before extending back through the fibrous construct 106 from the first side 102 to the second side 104 (after arrow 150). At arrow 152, the first filament body 110 completes the first loop configuration 130.

The first filament body 110 can also form the second loop configuration 132 in the second section 122. In one implementation, the first filament body 110 will continue as a single monolithic structure across the mid-plane 118 to penetrate through the fibrous construct 106, as noted more below. Other implementations may terminate the first filament body 110 in lieu of a second filament body (not shown) that interleaves with the fibrous construct 106 in the second section 122. Each of the first filament body 110 and the second filament body (not shown) may couple with the fibrous construct 106 using a suitably configured knot or other structure (or fixation technique) to prevent movement of the respective filament body relative to the fibrous construct 106 during manufacture, preparation, and deployment of the suture anchor 100.

Continuing in the direction from left to right in the diagram of FIG. 4, and starting at arrow 154, the first filament body 110 extends through the fibrous construct 106 from the second side 104 to the first side 102. Following arrow 156 to arrow 158, the filament body 110 forms the center loop 136 and extends back through the fibrous construct 106 from the first side 102 to the second side 104. At arrow 160, the first filament body 110 traverses along the longitudinal axis 116 of the fibrous construct 106 on the second side 104 until again extending from the second side 104 to the first side 102. In this example, as indicated by arrow 162 and arrow 164, the first filament body 110 inserts into the center loop 136 to form the threader loop 134 before extending back through the fibrous construct 106 from the first side 102 to the second side 104 (after arrow 164). Continuing to arrow 166, the first filament body 110 then extends through the fibrous construct 106 from the second side 104 to the first side 102 to form the second free-end 128 of the first filament body 110.

Figure 5:
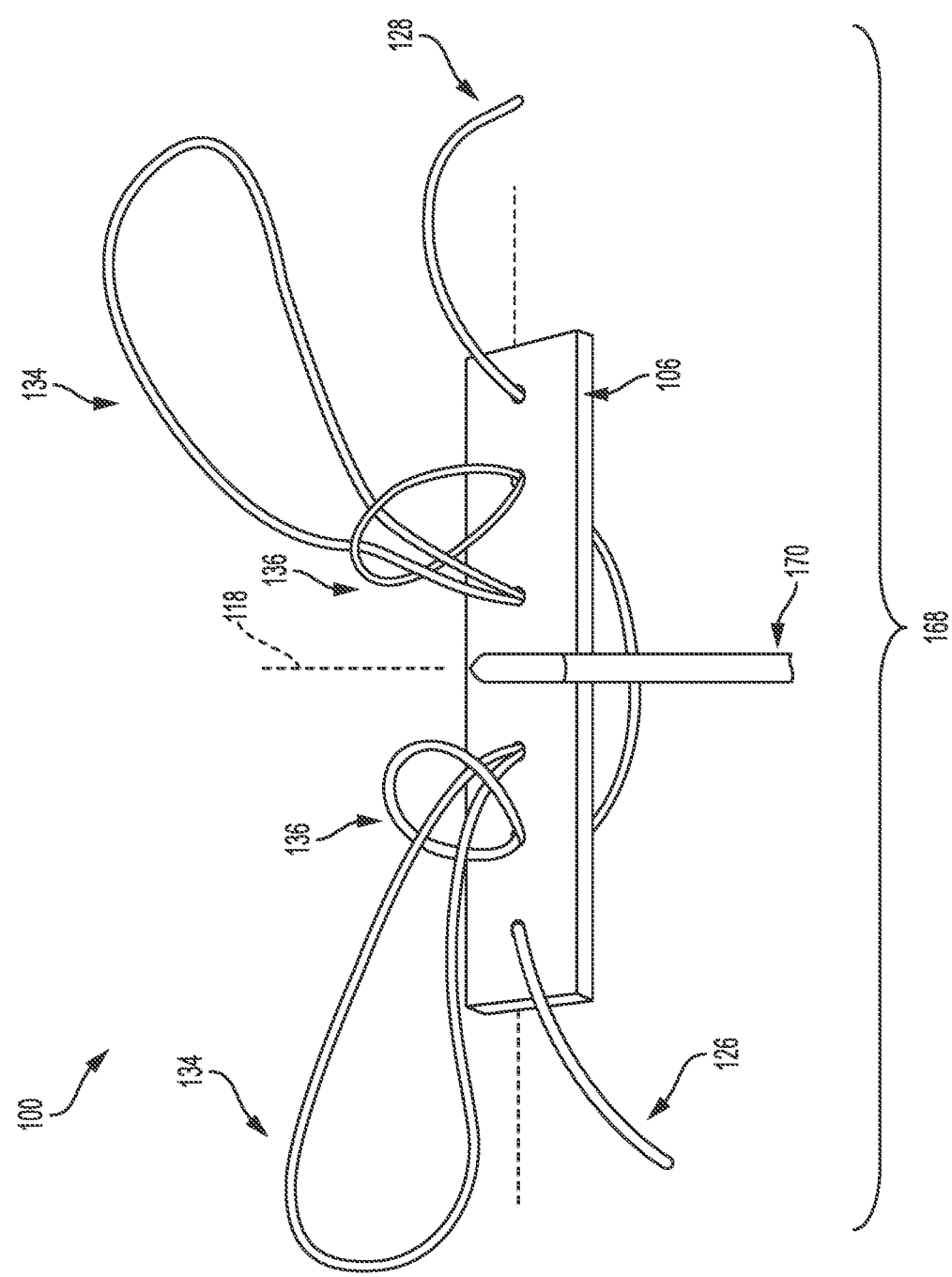
FIG. 5 represents a front, perspective view of an exemplary embodiment of a suture anchor as part of a suture anchoring system in accordance with an embodiment.

Referring now to FIGS. 5, 6, 7, 8, and 9, the discussion turns to describe use and deployment of the suture anchor 100. FIG. 5 illustrates a front, perspective view of the suture anchor 100 in assembled form. The suture anchor 100 is part of an anchoring system 168 (also, "kit 168") that includes insertion tooling 170. The anchoring system 168 is configured with the suture anchor 100 pre-loaded on the insertion tooling 170. This configuration facilitates use of the suture anchor 100 during surgery. In one implementation, insertion tooling 170 engages the fibrous construct 106 at or around the mid-plane 118. As mentioned above, the threading pattern arranges the first filament body 110 so that the threader loops 134 are much larger (or longer) than the center loops 136. This configuration provides sufficient slack to allow the threader loops 134 to extend out of the pre-formed hole at the fixation site.

Figure 6:
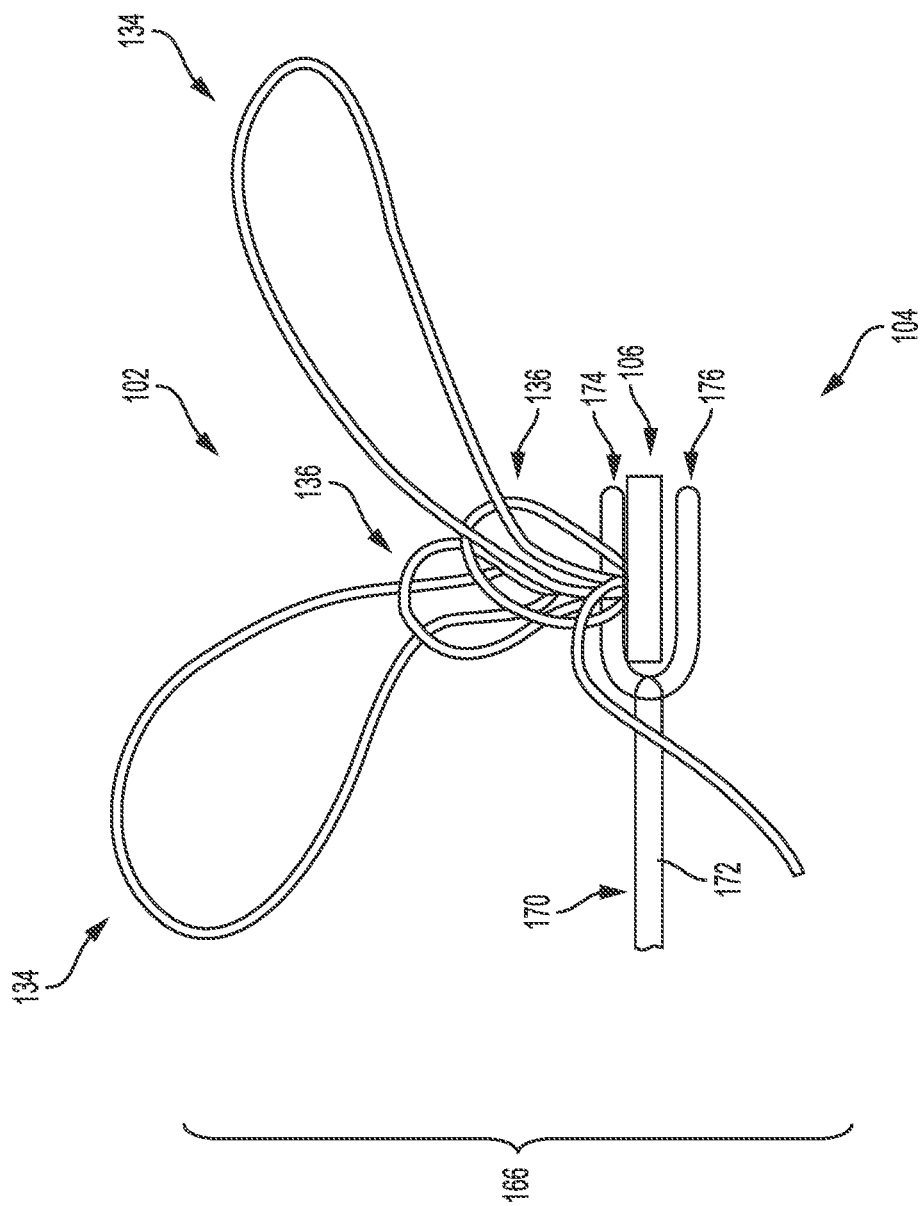
FIG. 6 represents a side view of an exemplary embodiment of a suture anchor as part of a suture anchoring system in accordance with an embodiment.

Referring now to FIG. 6, there is shown a side, elevation view of the anchoring system 168. The insertion tooling 170 has an elongated shaft member 172 that terminates at a pair of actuatable forks (e.g., a first actuatable fork 174 and a second actuatable fork 176). The forks 174, 176 are configured to move relative to one another in response to actuation at a handle, trigger, or other actuating member on the insertion tooling 170 that couples with the forks 174, 176. In use, the forks 174, 176 are positioned on either side 102, 104 of the fibrous construct 106. The insertion tooling 170 is configured to affect a positive "clamping" force that biases the forks 174, 176 toward one another. This clamping force releaseably secures the fibrous construct 106 between the forks 174, 176 prior to full deployment of the suture anchor 100.

Figure 7:
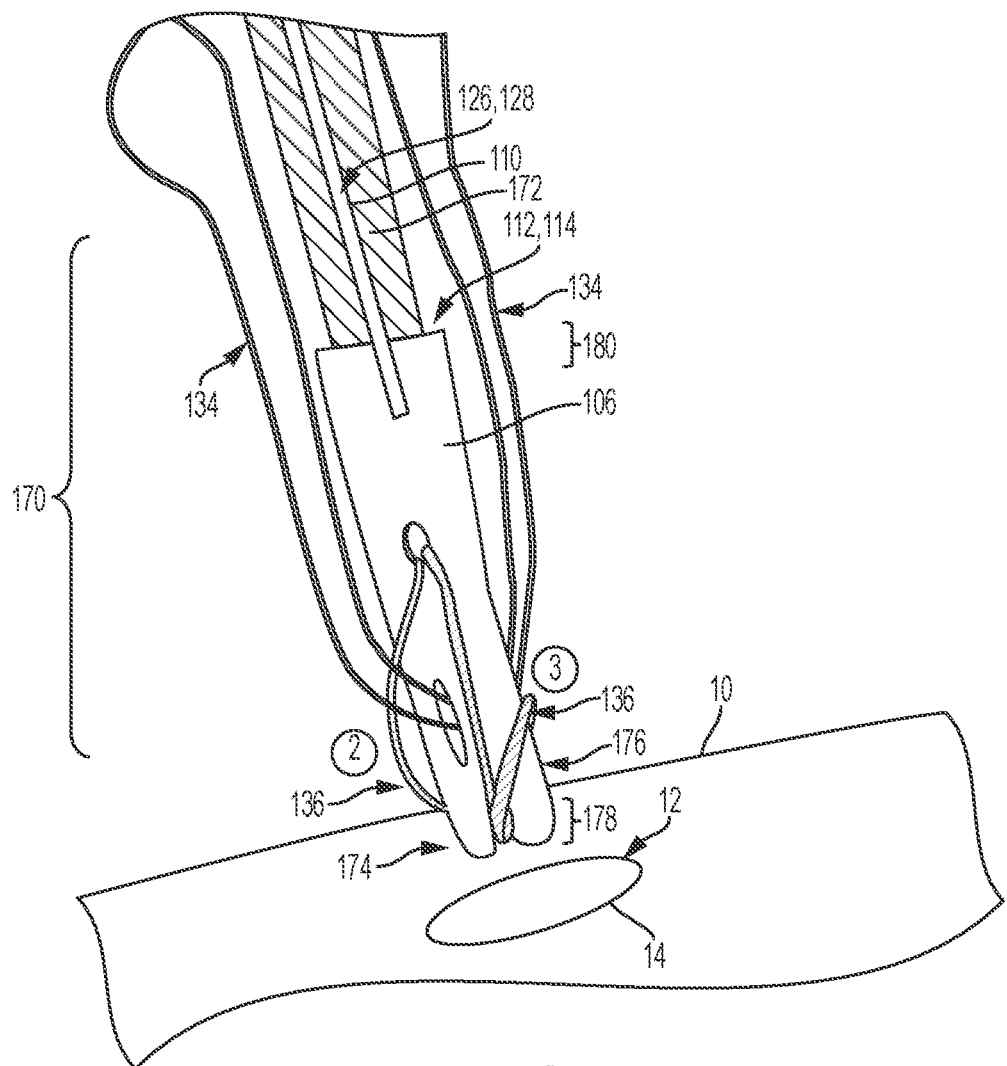
FIG. 7 represents a perspective view of an exemplary embodiment of a suture anchor as part of a suture anchoring system in position proximate a pre-formed hole in boney matter in accordance with an embodiment.
Figure 8:
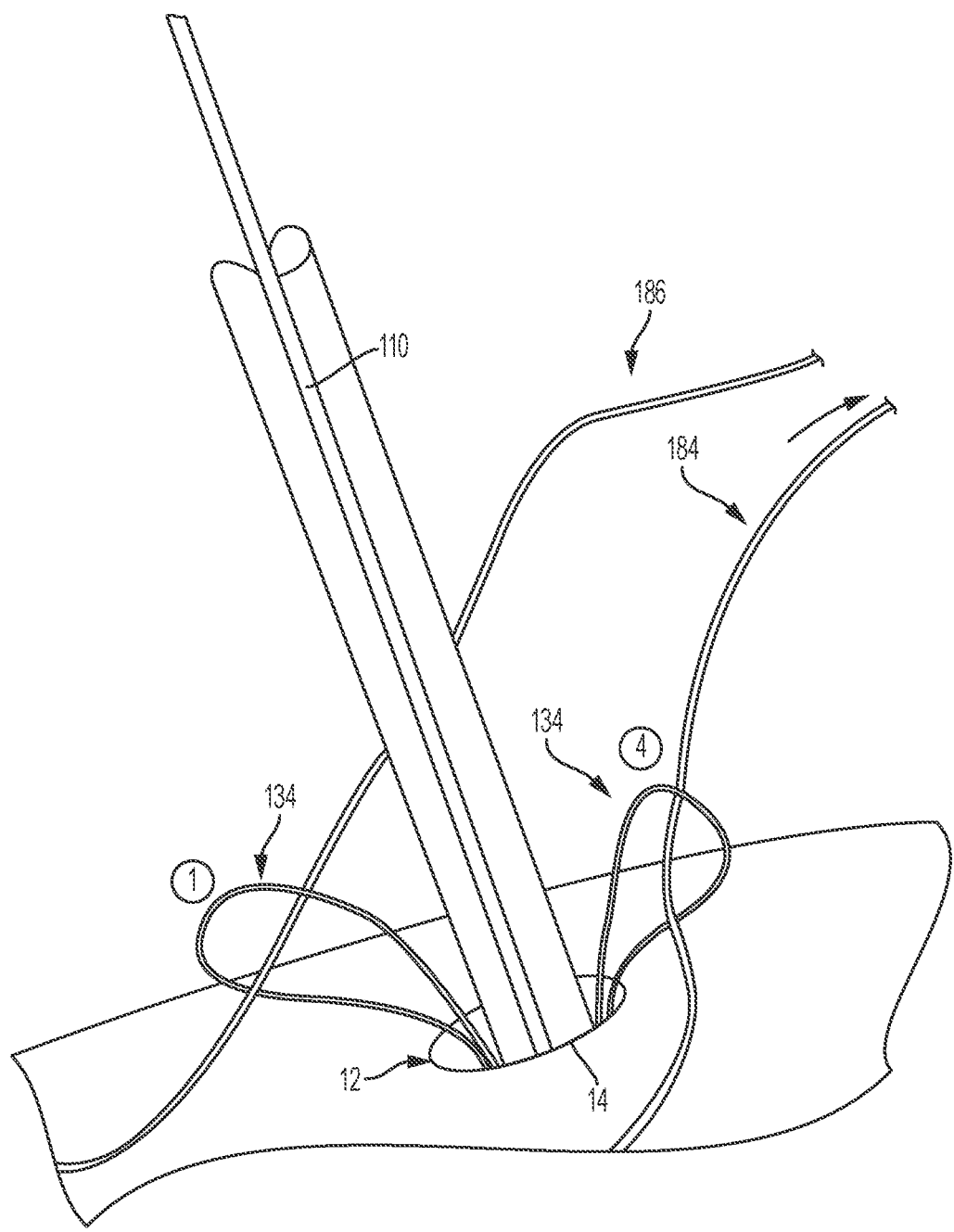
FIG. 8 represents a perspective view of an exemplary embodiment of a suture anchor as part of a suture anchoring system disposed in a pre-formed hole in boney matter in accordance with an embodiment.
Figure 9:
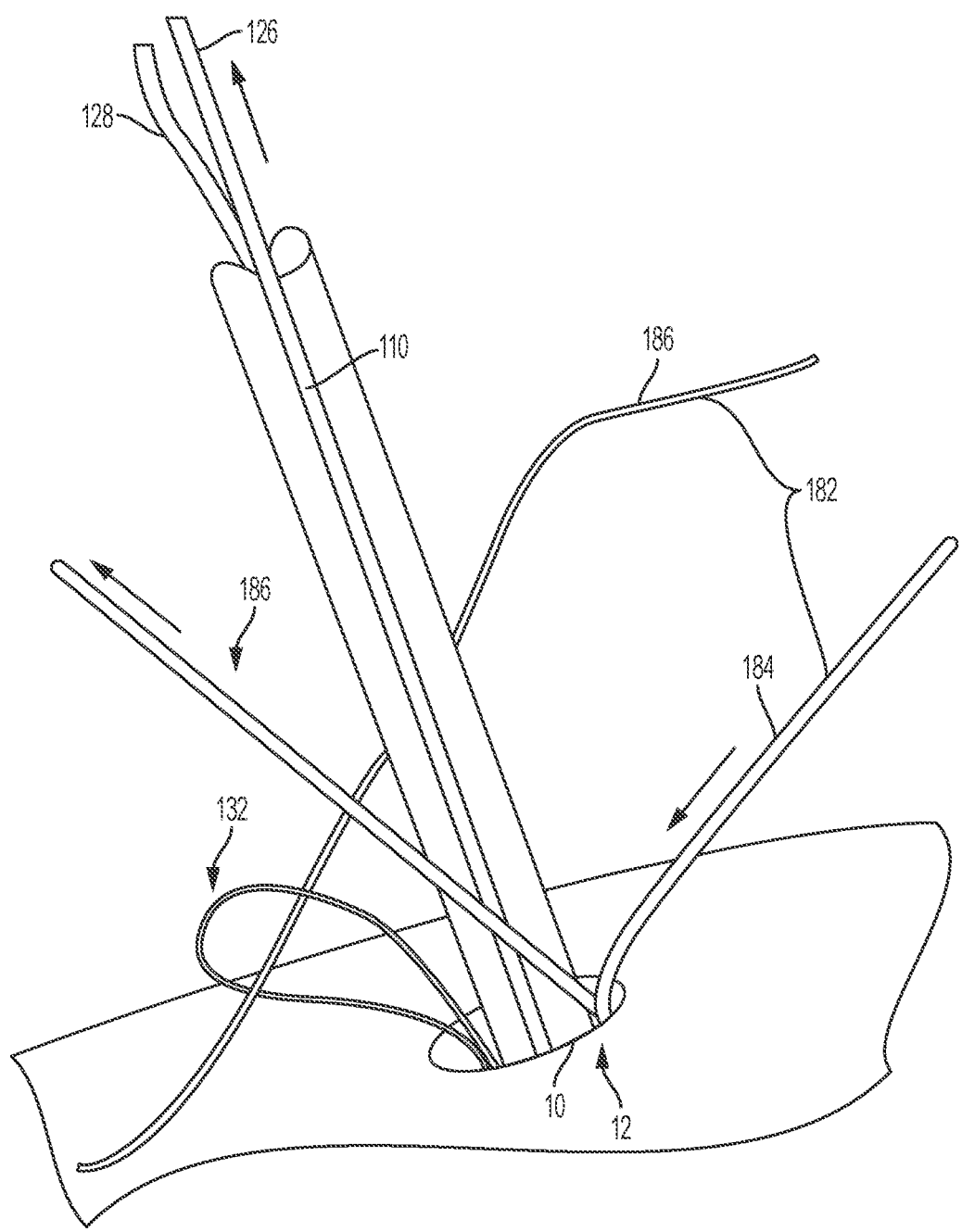
FIG. 9 represents a perspective view of an exemplary embodiment of a suture anchor as part of a suture anchoring system disposed in a pre-formed hole in boney matter and in a partially deployed state in accordance with an embodiment.

Referring now to FIGS. 7, 8, and 9, there is shown the anchoring system 168 in use at a repair site during an exemplary surgical procedure. In FIG. 7, the repair site is found at a boney member 10 with a pre-formed hole 12 featuring an opening 14 of generally fixed diameter. The suture anchor 100 assumes a pre-loaded configuration with the fibrous construct 106 firmly secured by the forks 174, 176 of the insertion tooling 170. This pre-loaded configuration is consistent with the state of the anchoring system 168 just prior to unbagging for use during the surgical procedure. In one implementation, the fibrous construct 106 is collapsed over the insertion tooling 170 to locate parts and/or portions of at least one side 102, 104 (FIGS. 5 and 6) of the fibrous construct 106 in close proximity and/or contact with the shaft member 172. The collapse of the fibrous construct 106 sizes the suture anchor 100 to easily fit within the fixed diameter of the pre-formed hole 12.

As also shown in FIG. 7, the preloaded configuration orients the suture anchor 100 with a distal end 178 and a proximal end 180. The distal end 178 corresponds with portions of the fibrous construct 106 proximate the forks 174, 176; in use, these portions of the fibrous construct 106 insert first into the pre-formed hole 12. At the proximal end 180, the ends 112, 114 of the fibrous construct 106 are spaced away from the boney member 10. The free ends 126, 128 of the first filament body 110 extend from the passing locations 124 (FIGS. 2, 3, and 4) near the ends 112, 114 and away from the boney member 10. The free ends 126, 128 may be under tension to collapse (or maintain the collapse) of the fibrous construct 106.

The pre-loaded configuration may also couple the center loops 136 with the insertion tooling 170. In one implementation, the center loops 136 are in a position that secures one of the center loops 136 of each loop configuration 130, 132 (FIG. 3) to one of the forks 174, 176, respectively. This position is helpful to provide the surgeon with a "positive" tactile indication (or "pop"). During operation, for example, the center loops 136 will disengage off of the respective fork 174, 176 in response to tension applied to free ends 126, 128 of the first filament body 110.

FIG. 8 shows the anchoring system 168 with the suture anchor 100 disposed in the pre-formed hole 12 and out of view in the diagram. The repair site includes a repair suture 182 with one or more repair ends (e.g., a first repair end 184 and a second repair end 186). The repair ends 184, 186 are generally free and originate from the adjacent fixation site (not shown) that secures the repair suture 180 to the boney member 10. As mentioned above, at least a portion of the threader loops 134 remain exposed to receive the repair ends 184, 186 with one of the repair ends 184, 186 extending into and through one of threader loops 134, respectively.

FIG. 9 shows the anchoring system 168 in a partially deployed state that results from tension on one of the free-ends 126, 128 of the first filament body 110. In FIG. 9, applying tension T to the free-end 126 tightens the threader loop 134 of the first loop configuration 126 (FIG. 3), which is no longer in view in the diagram of FIG. 9. The threader loop 134 draws the repair end 184 of the repair suture 182 into the pre-formed hole 12. Although not shown, applying tension T to the free-end 128 tightens the threader loop 134 of the second loop configuration 128 (FIG. 3) draws the repair end 186 into the pre-formed hole 12.

Figure 10:
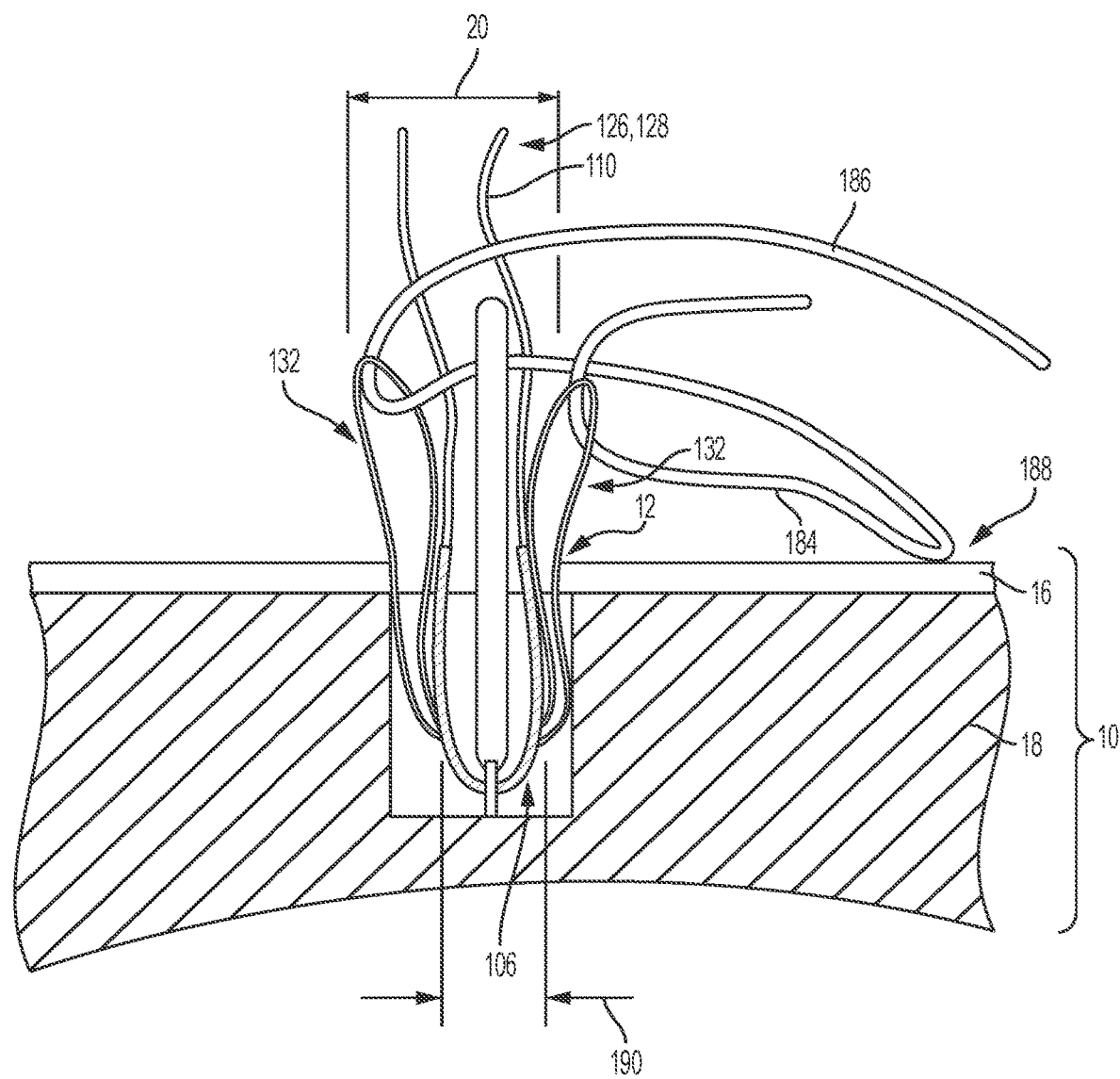
FIG. 10 represents an elevation view of the cross-section of an exemplary embodiment of a suture anchor as part of a suture anchoring system disposed in a pre-formed hole in boney matter and in an un-deployed state in accordance with an embodiment.
Figure 11:
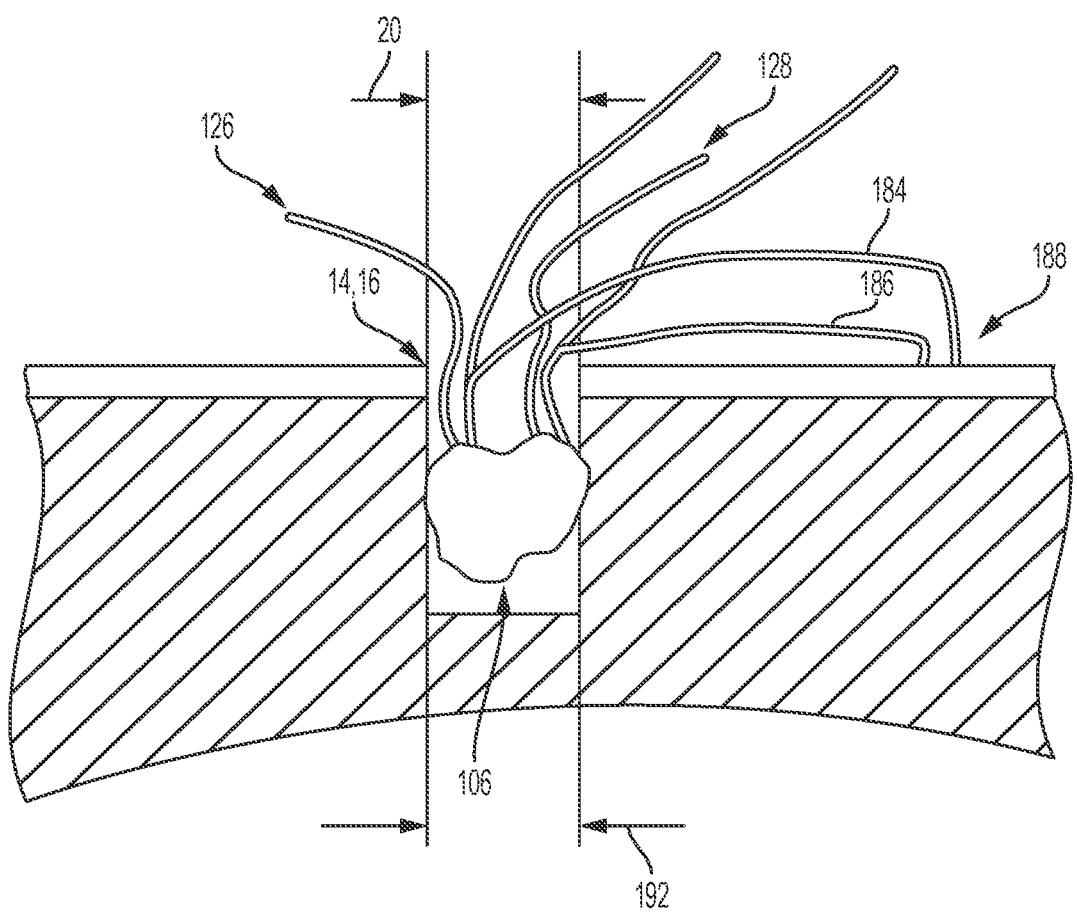
FIG. 11 represents an elevation view of the cross-section of an exemplary embodiment of a suture anchor as part of a suture anchoring system disposed in a pre-formed hole in boney matter and in a deployed state in accordance with an embodiment.

Referring now to FIGS. 10 and 11, there is shown an elevation view of a cross-section of an example of a repair site. FIG. 10 illustrates the suture anchor 100 in an example of an un-deployed state. FIG. 11 illustrates the suture anchor 100 in an example of a fully deployed state, after the partially deployed state that locks the repair ends 184, 186 and typical of the suture anchor 100 as left upon completion of the surgical procedure.

In FIG. 10, the repair suture 182 originates from a primary fixation site 188 that is spaced apart from the pre-formed hole 12. The boney member 10 is shown with a first or cortical layer 16 and a second or cancellous layer 18. The pre-formed hole 12 penetrates into both layers 16, 18, with the opening 14 disposed primarily in the upper cortical layer 16. The walls of the pre-formed hole 12 are formed primarily of the lower cancellous layer 18. As also shown in FIG. 10, the pre-formed hole 12 defines a pre-formed area 20. Because the cortical layer 16 is hard, the pre-formed area 20 is generally fixed in size and shape. On the other hand, the cancellous layer 18 is soft (at least relative to the cortical layer 16), which allows the pre-formed area 20 to vary in response to changes in the state of the suture anchor 100.

When collapsed over the shaft member 172 in the preloaded configuration, the suture anchor 100 has a first effective area 190 that allows the suture anchor 100 to pass through and insert into the opening 14. The first effective area 190 may be smaller than the pre-formed area 20, particularly at the opening 14 in the cortical layer 16, although such configuration may not always be the case because the malleable nature of the fibrous construct 106 may allow for insertion of the suture anchor 100 independently of the relationship between the first effective area 190 and the pre-formed area 20 of the pre-formed hole 14.

As best shown in FIG. 11, the suture anchor 100 is configured with a second effective area 192 that is larger than the first effective area 190. The second effective area 192 is also larger than the pre-formed area 20 and, thus, is unable to pass through the opening 14 of the pre-formed hole 12 in the hard, cortical layer 16 of the boney member 10. This configuration can also cause the suture anchor 100 to contact the walls of the pre-formed opening 12. Preferably, the second effective area 192 is sized so that the suture anchor 100 grips and/or even laterally displaces some of the cancellous layer 18 that forms the walls of the pre-formed hole 12.

Figure 12:
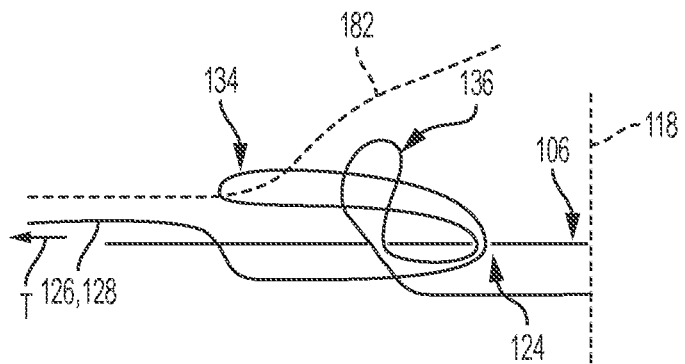
FIG. 12 represents a schematic diagram of an exemplary embodiment of a suture anchor in accordance with an embodiment.
Figure 13:
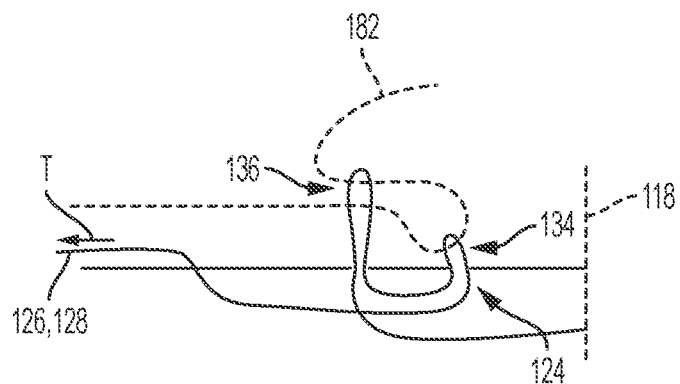
FIG. 13 represents a schematic diagram of an exemplary embodiment of a suture anchor in accordance with an embodiment.
Figure 14:
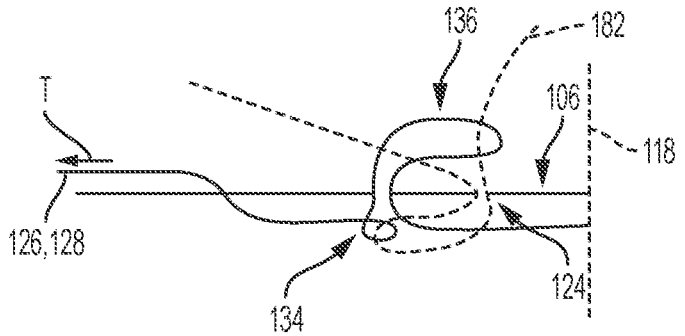
FIG. 14 represents a schematic diagram of an exemplary embodiment of a suture anchor in accordance with an embodiment.
Figure 15:
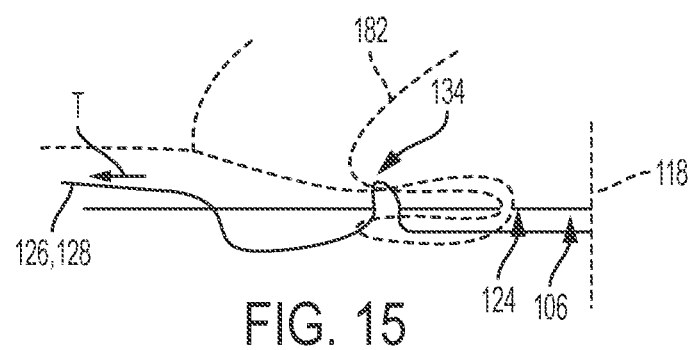
FIG. 15 represents a schematic diagram of an exemplary embodiment of a suture anchor in accordance with an embodiment.

Referring now to FIGS. 12, 13, 14, and 15 there are shown schematic diagrams of the suture anchor 100 to further illustrate the operation of the suture anchor 100. The schematic diagrams illustrate movement of the first filament body 110 to form the repair suture 182 into the tortuous path and also to integrate the repair suture 182 into the fibrous construct 106. FIG. 12 depicts the suture anchor 100 and repair suture 182 in a ready position for the surgeon to apply tension T to the free-end 126, 128 of the first filament body 110. FIG. 13 shows the threader loop 134 pulling the repair suture 182 through the center loop 136 and down towards the passing location 124 nearest the mid-plane 118. In FIG. 14, under continued tension to the free-end 126, 128, the center loop 136 bends downward towards the fibrous construct 106. In FIG. 15, the center loop 136 locks the repair suture 180 into position on the fibrous construct 106.

While embodiments of the present invention has been particularly shown and described with reference to certain exemplary embodiments, it will be understood by one skilled in the art that various changes in detail may be effected therein without departing from the spirit and scope of the invention as defined by claims that can be supported by the written description and drawings. Further, where exemplary embodiments are described with reference to a certain number of elements it will be understood that the exemplary embodiments can be practiced utilizing either less than or more than the certain number of elements.

What is claimed is:

1. A suture anchor, comprising:
a fibrous construct formed of ultra-high molecular weight polyethylene (UHMW) and having a first surface, a second surface opposing the first surface, a third surface, a fourth surface, a fifth surface, and a sixth surface, wherein each of the first surface and the second surface has a larger surface area than the third, fourth, fifth, and sixth surfaces, wherein the first surface is opposite the second surface, the third surface is opposite the fifth surface and the fourth surface is opposite the sixth surface, wherein each of the fourth surface and the sixth surface extends in a plane parallel to a central longitudinal axis, a width extending across the first surface and the central longitudinal axis extending along the first surface wherein the central longitudinal axis is located central with respect to the width; and
a plurality of holes formed through the fibrous construct from the first surface to the second surface including a first hole, a second hole, a third hole, a fourth hole, a fifth hole and a sixth hole wherein the first hole, the second hole, the third hole, the fourth hole, the fifth hole and the sixth hole are each substantially positioned in spaced apart relation along a first longitudinal axis from the third surface to the fifth surface and extending through the first surface and the second surface; and
a first filament body comprising a first end and a second end, wherein the first filament body is positioned in a first configuration with respect to the fibrous construct wherein the first configuration comprises:
from the first end to the second end, the first filament body extends to and passes through the third hole from the second surface to the first surface and forms a first loop of a first pair of loops, extends back to and through the third hole from the first surface to the second surface, extends to and passes through the second hole from the second surface to the first surface and forms a second loop of the first pair of loops, wherein the first pair of loops interleave with one another; and
the first filament body extends from forming the second loop through the second hole from the first surface to the second surface, extends to and passes through the fifth hole from the second surface to the first surface and forms a third loop of a second pair of loops, extends back to and through the fifth hole from the first surface to the second surface, extends to and passes through the fourth hole from the second surface to the first surface and forms a fourth loop of the second pair of loops, wherein the second pair of loops interleave with one another.

2. The suture anchor of claim 1, wherein the second hole is disposed closer to a mid-plane of the fibrous construct than the first hole.

3. The suture anchor of claim 1, wherein the second end of the first filament body extends through the sixth hole to form a free-end.

4. The suture anchor of claim 1, wherein the fibrous construct is selected from a group consisting of a woven fabric, an unwoven fabric, a braid, and a knitted fabric.

5. The suture anchor of claim 1, wherein the fibrous construct comprises material that is collapsible without tearing.

6. The suture anchor of claim 1, wherein the first longitudinal axis is the central longitudinal axis.

7. The suture of claim 6, wherein the first filament body exits the fibrous construct by passing through the sixth hole from the second surface to the first surface.

8. The suture anchor of claim 1, wherein the first filament body enters the fibrous construct by passing through the first hole from the first surface to the second surface.

9. A suture anchor, comprising: a substrate formed of ultra-high molecular weight polyethylene (UHMW) and having a first surface, a second surface opposing the first surface, a third surface, a fourth surface, a fifth surface, and a sixth surface, wherein each of the first surface and the second surface has a larger surface area than the third, fourth, fifth, and sixth surfaces, a width extending across the first surface and a central longitudinal axis extending along the first surface wherein the central longitudinal axis is located central with respect to the width; and a filament comprising a first end and a second end interwoven into the substrate in a first configuration, wherein the first configuration comprises the filament, from the first end to the second end, extending through the substrate at first and second passing locations, respectively, on a first surface of the substrate to form a first loop and a second loop, wherein the filament first enters the substrate at the second passing location, wherein the second passing location is closer to a medial position of the substrate than the first passing location, and the filament passes through the first passing location after passing through the second passing location, wherein the first loop extends through the second loop and is configured to receive a repair suture therein, and a third loop and a fourth loop formed through a third and a fourth passing locations, respectively, on the first surface of the substrate, wherein the third loop extends through the fourth loop on the same surface of the substrate as the first loop and the second loop, and wherein the first passing location, the second passing location, the third passing location and the fourth passing location are each substantially positioned in spaced apart relation along a first longitudinal axis.

10. The suture anchor of claim 9, wherein the first loop is longer than the second loop.

11. The suture anchor of claim 9, wherein the substrate and the filament can assume a first state and a second state that is different from the first state, and wherein the first state configures the substrate to fit within a pre-formed hole in bone and the second state configures the substrate with an effective area that is larger than the effective area of an opening of the pre-formed hole.

12. The suture anchor of claim 9, wherein the first longitudinal axis is the central longitudinal axis.

13. A suture anchoring system, comprising: a suture anchor comprising a fibrous construct formed of ultra-high molecular weight polyethylene (UHMW) and having a first surface, a second surface opposing the first surface, a third surface, a fourth surface, a fifth surface, and a sixth surface, wherein each of the first surface and the second surface has a larger surface area than the third, fourth, fifth, and sixth surfaces, a width extending across the first surface and a central longitudinal axis extending along the first surface wherein the central longitudinal axis is located central with respect to the width, and having a filament comprising a first end and a second end disposed in a loop configuration with a first loop formed through a first hole on a first surface of a fibrous construct and extending through a second loop formed through a second hole on the first surface of the fibrous construct and a third loop formed through a third hole on the first surface of the fibrous construct and extending through a fourth loop formed through a fourth hole on the first surface of the fibrous construct, wherein the filament first enters the fibrous construct at the second hole, wherein the second hole is closer to a medial position of the substrate than the first hole, and the filament, from the first end to the second end, passes through the first hole after passing through the second hole in the loop configuration, the suture anchor having an un-deployed state and a deployed state in which the width of the suture anchor is different than the width of the suture anchor in the un-deployed state; and insertion tooling coupled with the suture anchor, and wherein the first hole, the second hole, the third hole and the fourth hole are each substantially positioned in spaced apart relation along a first longitudinal axis.

14. The suture anchoring system of claim 13, wherein one of the loops in the loop configuration engages part of the insertion tooling in the un-deployed state.

15. The suture anchoring system of claim 13, wherein the insertion tooling comprises a pair of actuatable forks, and wherein the second loop is disposed on one of the pair of actuatable forks.

16. The suture anchoring system of claim 13, wherein the fibrous construct comprises material that configures the suture anchor to collapse around the insertion tooling.

17. The suture anchoring system of claim 13, wherein the width of the suture anchor in the un-deployed state configures the suture anchor to insert into a pre-formed hole in bone, and wherein the width of the suture anchor in the deployed state secures the suture anchor within the pre-formed hole.

18. The suture anchoring system of claim 13, wherein the first longitudinal axis is the central longitudinal axis.

* * * * *